(12) United States Patent
Leight

(10) Patent No.: US 6,299,019 B1
(45) Date of Patent: Oct. 9, 2001

(54) HOLLOW HANDLE EARPLUG DISPENSER

(75) Inventor: Howard S. Leight, Malibu, CA (US)

(73) Assignee: Leight Industries, San Diego, CA (US)

( * ) Notice: Subject to any disclaimer, the term of this patent is extended or adjusted under 35 U.S.C. 154(b) by 0 days.

(21) Appl. No.: 09/564,728

(22) Filed: May 3, 2000

Related U.S. Application Data

(60) Provisional application No. 60/147,437, filed on Aug. 5, 1999.

(51) Int. Cl.$^7$ .................................................. A24F 15/04
(52) U.S. Cl. ........................................ 221/186; 221/265
(58) Field of Search .................................. 221/265, 277, 221/282, 263, 155, 197, 186, 188

(56) References Cited

U.S. PATENT DOCUMENTS

| | | |
|---|---|---|
| 1,321,385 | 11/1919 | Millard . |
| 1,982,273 | 11/1934 | Vogel et al. . |
| 2,330,256 | 9/1943 | Ashton . |
| 2,649,994 | 8/1953 | Lewis et al. . |
| 2,664,223 | 12/1953 | Dobkin . |
| 3,128,011 | 4/1964 | Bleiman . |
| 3,330,442 | 7/1967 | O'Connor . |
| 5,322,185 | 6/1994 | Leight . |
| 5,443,179 | 8/1995 | Palmer et al. . |
| 5,954,229 | 9/1999 | Scholey et al. . |

FOREIGN PATENT DOCUMENTS

WO 94/09456    4/1994  (WO) .

*Primary Examiner*—Kenneth W. Noland
(74) *Attorney, Agent, or Firm*—Leon D. Rosen

(57) ABSTRACT

An earplug dispenser is provided, which is of simple construction and which is easily operated by a person to dispense one or two earplugs with minimal possibility of the earplug bouncing off the person's hand and onto a dirty floor. The earplug dispenser includes a barrier (26) lying on a stand, a wheel (20) with earplug-receiving holes (22) rotatably mounted above the barrier, and a handle device (28) fixed to the wheel and lying below the barrier. As the handle device is turned about a vertical axis (60), earplugs in the wheel holes move over a dispense aperture (42) in the barrier and fall through it and through the handle device onto the palm of a person who is turning the handle device. The handle device includes a largely cylindrical handle (72) that encourages the handle to be held with the palm (P) closely under the open lower end (44) of the handle and with the fingers of the person extending up along vertical grooves (82) in the handle, so earplugs fall into the person's palm. The stand (16) has a catch pad (74) at the bottom and has an access opening (76) of less than 180° to further reduce the possibility of loss of the earplug. The barrier is in the form of an upside-down cap with an internal thread (106). A container (12) that holds numerous earplugs, has a lower end with threads (102) that screw into the cap.

11 Claims, 5 Drawing Sheets

US 6,299,019 B1

HOLLOW HANDLE EARPLUG DISPENSER

CROSS-REFERENCE

Applicant claims priority from provisional patent application 60/147,437 filed Aug. 05, 1999.

BACKGROUND OF THE INVENTION

This invention is a simple earplug dispenser which can receive a container with many earplugs and dispense them one or two at a time as a person turns a handle.

Devices for dispensing one item at a time, such as pills, sometimes use a wheel that is rotated by a person's hand, with the wheel having holes that receive the items and that move the items over an opening in a barrier so the items fall into the person's hand. U.S. Pat. No. 2,649,994 shows a tablet dispenser of this construction. This general approach has been applied to earplug dispensers, as described in applicant's earlier application PCT/US93/09801 (WO 94/09456). While tablets are rigid, earplugs are generally elastomeric, so they tend to "bounce". As a result, an earplug can easily bounce off a person's palm onto the floor, or bounce off a catch pad lying under a dispense location and onto the ground. In factories where large numbers of earplugs are used, the floor is often dirty, as with oil carried to the location by the workers' shoes, so an earplug that drops onto the ground is generally considered dirty and thrown away. A dispenser that minimized the possibility of any dispensed earplug bouncing and falling onto the ground, while enabling earplugs to be readily dispensed in a simple mechanism, would be of value.

SUMMARY OF THE INVENTION

In accordance with one embodiment of the present invention, an earplug dispenser is provided, which is of simple construction and easy operation, and which minimizes the possibility of loss of a dispensed earplug by accidental dropping of the earplug onto the ground. The dispenser includes a wheel with a plurality of earplug-receiving holes, that rotates about a vertical axis above a barrier wall. As the wheel rotates, the earplugs drop out of the wheel holes and down through a dispense aperture in the barrier wall. A handle device lying below the barrier wall, is fixed to the wheel to rotate it, and has a handle with a hollow vertical passage to direct the fallen earplugs into the palm of a hand that is rotating the handle. The handle has a vertical height that is more than half the handle diameter, to encourage a person to rotate the wheel by placing his/her palm under the open bottom of the handle and with the fingers extending upwardly along the handle. This increases the possibility that any earplug bouncing off the person's palm, will not fall out of the palm.

The barrier is mounted on a stand that extends around and below the handle. A catch pad at the bottom of the stand catches earplugs that have fallen out of the person's palm. The stand has an access opening through which a person can insert his/her hand. The access opening extends by less than 180°, so the closed walls of the stand extend more than 180° about the axis to help catch any earplugs that bounce off the palm and might otherwise fall onto the ground.

The barrier is preferably in the form of an upside-down cap with a threaded inside surface. A container that holds numerous earplugs, has an open lower end with an external thread that threads into the threads of the barrier, to close the bottom of the container and hold it in place.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
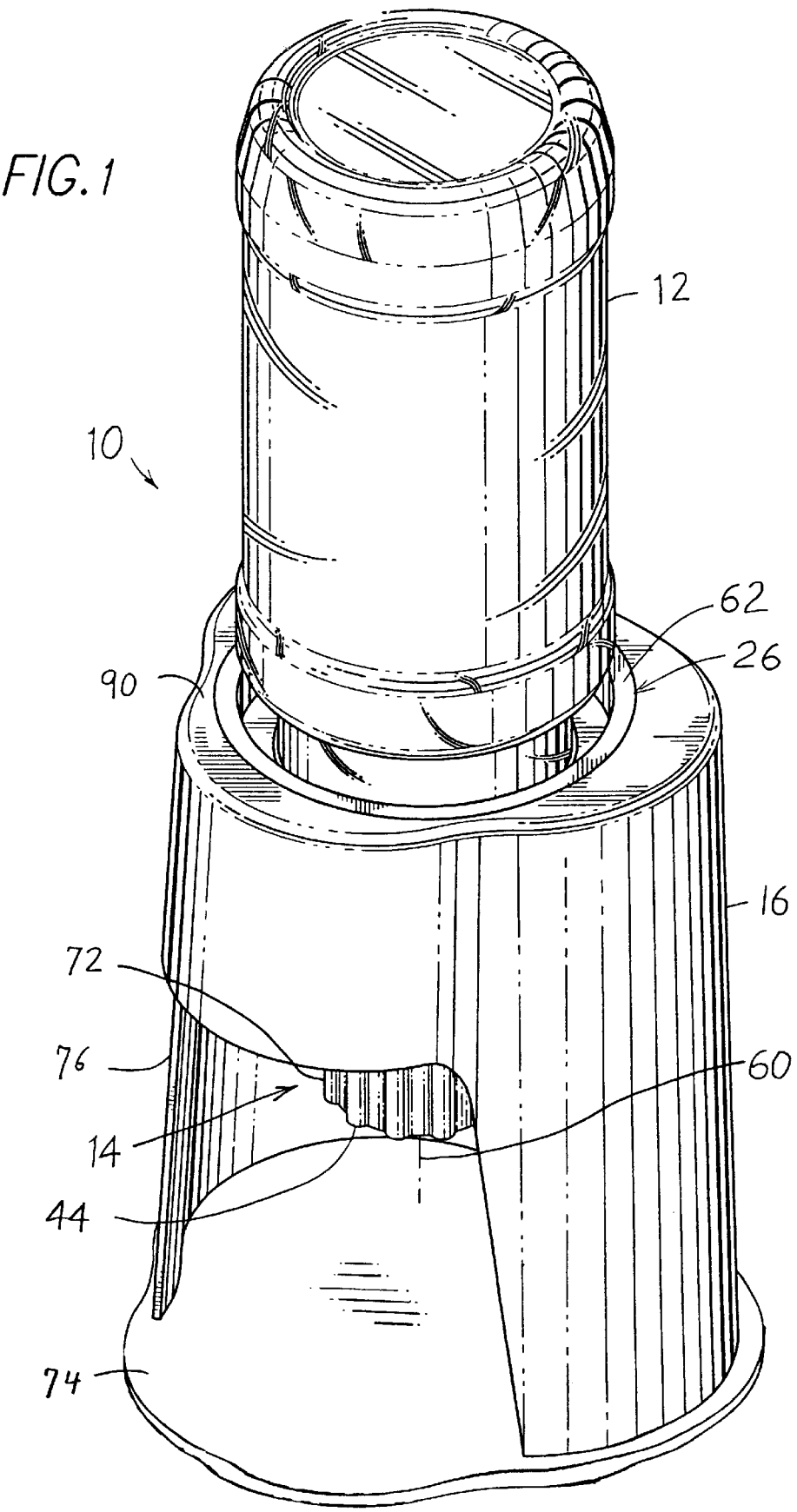
FIG. 1 is an isometric view of an earplug dispenser constructed in accordance with the present invention.

FIG. 1 illustrates an earplug dispenser 10 which includes a container 12 that contains numerous earplugs (hundreds of earplugs), a dispense mechanism 14 that can dispense one (or two) earplug(s) at a time, and a stand 16 that supports the dispense mechanism on a table or wall. A person projects his/her hand through an access opening 76 in the stand and turns a handle 72 about a vertical axis 60. As the handle is turned, an earplug drops out of an open lower end 44 of the handle after each 60° turn of the handle, in most cases.

Figure 2:
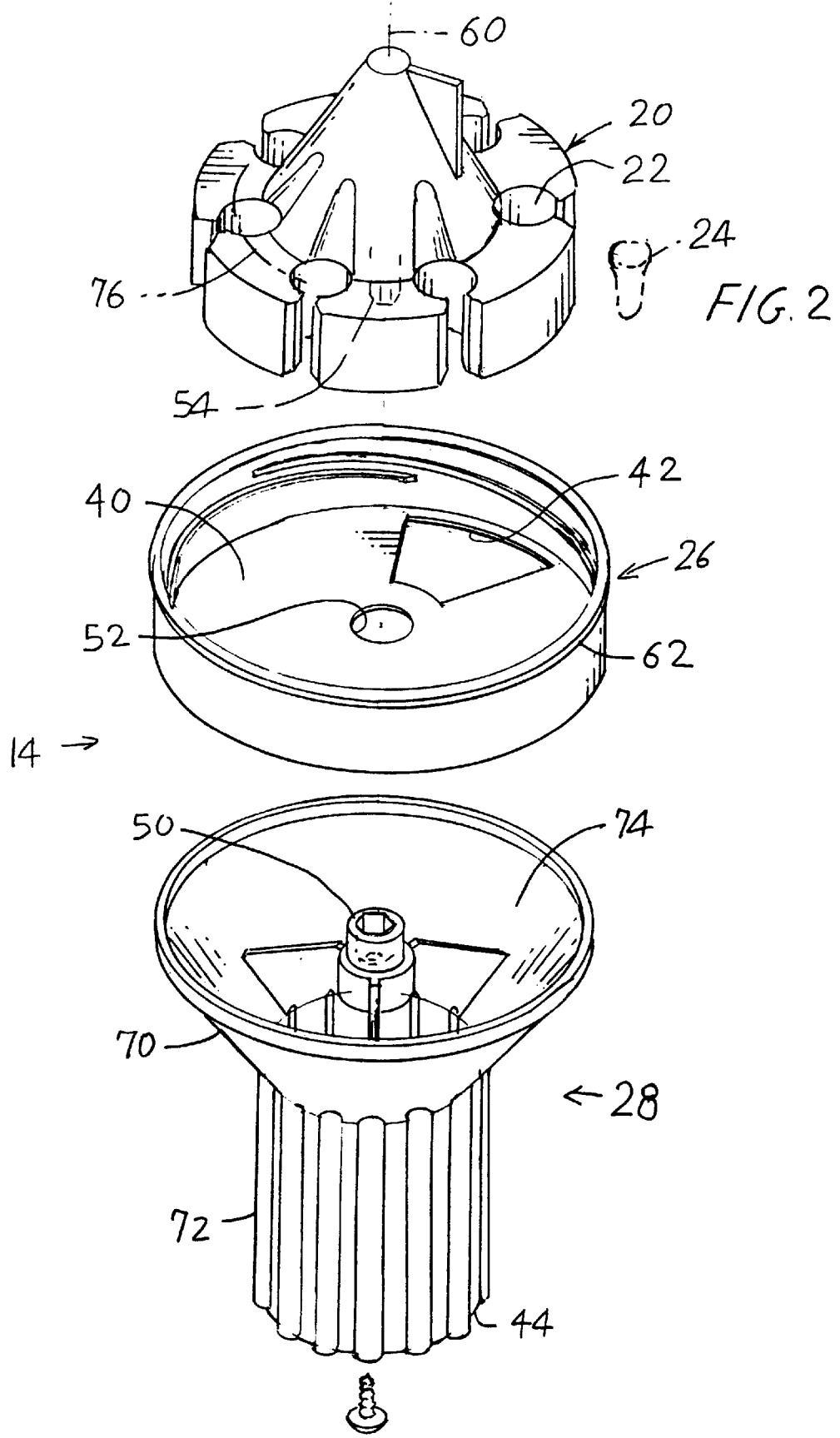
FIG. 2 is an exploded isometric view of the dispenser mechanism of the dispenser of FIG. 1.

FIG. 2 shows that the dispense mechanism 14 includes a wheel 20 with holes 22 that each can receive an earplug illustrated in phantom lines at 24, a barrier device or barrier 26, and a handle device 28 that includes the handle 72. The barrier 26 has a flat horizontal barrier wall 40 that lies under the holes 22 in the wheel to prevent an earplug that lies in one of the holes from falling out, until that hole has moved to a position over a dispense aperture 42 in the barrier wall. Then, the earplug in the hole 22 can fall through the aperture 42 and through the handle device 28 and out through the open lower end 44 of the handle device. The handle device has a primarily vertical through passage 74 that leads to the open lower end 44 of the handle. In most cases, the diameter of the circular path 76 of the holes 22 is greater than the diameter of the handle 72, so an upper portion of the handle device is formed as a funnel 70 that has a wide upper end to direct earplugs down to the narrower handle 72. It is also possible for the diameter of the circular path 76 of the holes to be slightly less than the diameter of the passage through the handle 72, so the funnel has vertical walls instead of tapered walls.

The handle device 28 includes a connector 50 that projects up through a hole 52 in the barrier device and connects to a shaft 54 on the wheel. As a result, when the handle device is turned about the vertical axis 60, it turns the wheel 20. However, the barrier device 26 does not turn. Instead, the barrier device has a lip 62 that rests on the stand 16 as shown in FIG. 1. Friction between the lip 62 and the stand is sufficient to prevent rotation of the barrier device 26 (or only slight and occasional rotation) when the handle and wheel 28, 20 of FIG. 2 turn.

Figure 4:
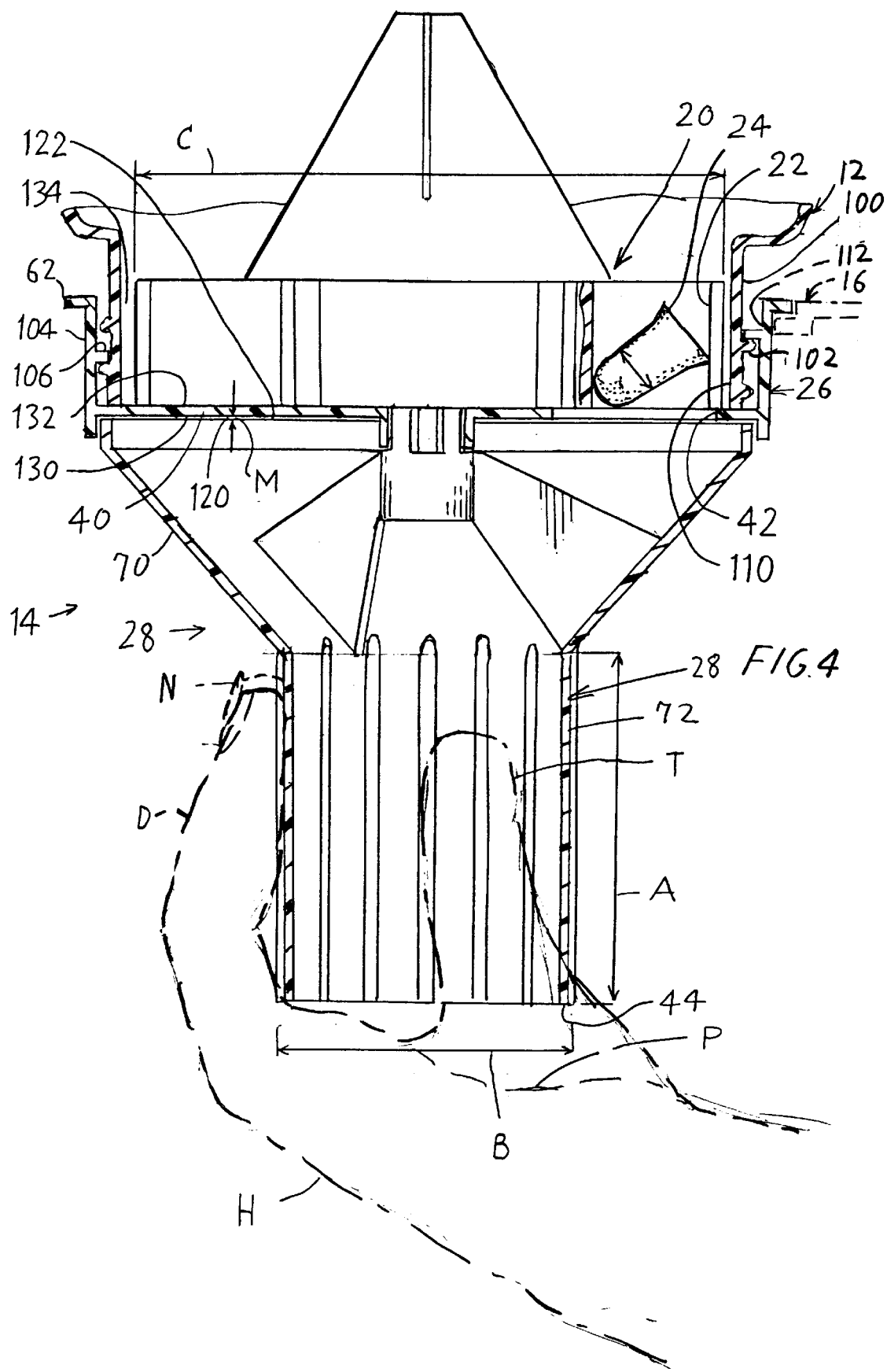
FIG. 4 is a sectional side view of the dispenser mechanism of FIG. 3, with the person's hand shown in phantom lines.
Figure 5:
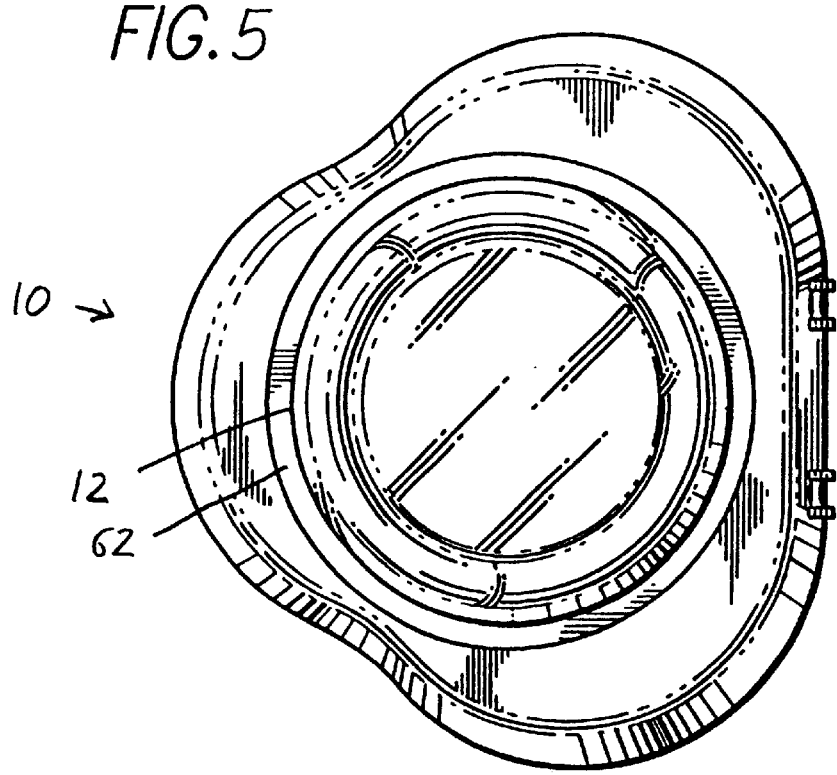
FIG. 5 is a plan view of the dispenser of FIG. 1.

FIG. 4 shows a hand H of a person grasping the handle 72 to turn it, so the handle device 28 and wheel 20 both turn. A new earplug is dispensed after every 60° in most cases, and after 120° in almost all cases. It is possible to turn the handle back and forth instead of continually in one direction, although instructions may tell the person to turn the wheel in one direction.

The handle 72 of a dispenser that applicant has constructed and successfully tested, has a height A of 6.5 cm and a diameter B of 6 cm. This compares to the diameter C of 11 cm for the wheel 20 and the diameter of 8.5 cm of the ring of earplug-receiving holes 22. Applicant has found that a handle diameter of about 6 cm enables a person to place his/her palm P against the open lower end 44 of the handle, and extend the fingers upwardly along the handle, with the thumb T, forefinger D, and middle finger N shown in FIG. 4, and with the little and ring fingers E, G shown in FIG. 3. Most or all of the fingers extend upwardly along the handle. With the fingers extending upwardly along the handle, a person can turn the handle and reliably catch any earplug that is falling down through the handle device, in the palm of the hand. Even though the earplug is elastomeric, there is only a small possibility that the earplug will bounce off the palm and fall on the floor. If an earplug should fall on the floor, then it is generally considered dirty, and an employee is likely to throw it away and take another earplug. By allowing and even encouraging the palm P of the hand to lie close to the open bottom 44 of the handle, applicant makes it easy for a person to grasp the handle to turn it, while avoiding loss of earplugs when they bounce off the palm.

As mentioned above, the handle shown in FIG. 4 has a height of 6.5 cm which allows a person to place his palm P against or close to the open lower end 44 of the handle while his/her fingers extend upwardly along the largely cylindrical handle. Applicant prefers that the largely cylindrical outside surface of the handle have a diameter of no more than 9 cm. If the diameter is more than about 9 cm, then the palm of the hand cannot cover substantially all of the open bottom end of the handle, and earplugs may fall out through a side. Also, with a diameter of much more than 9 cm, a person tends to place only the tips of his fingers against the outside of the handle, with his/her palm lying everywhere about an inch or more below the bottom of the open end, increasing the likelihood that an earplug will bounce off the palm and onto the floor. It is also desirable that the outside diameter of the handle be at least 4 cm, to avoid a person moving his fingertips close together to grasp the handle, and leaving his/her palm at least one half inch and usually more than one inch below the bottom of the open end of the handle. The height A of the handle is unlimited, but should be at least 4 cm to allow substantially the full lengths of all of the fingers to lie against the outside of the handle, so the palm lies closely under the lower end of the handle. In most cases, the handle height A is at least half the handle diameter B, to allow grasping the handle with the palm closing the open lower end 44 of the handle.

Figure 3:
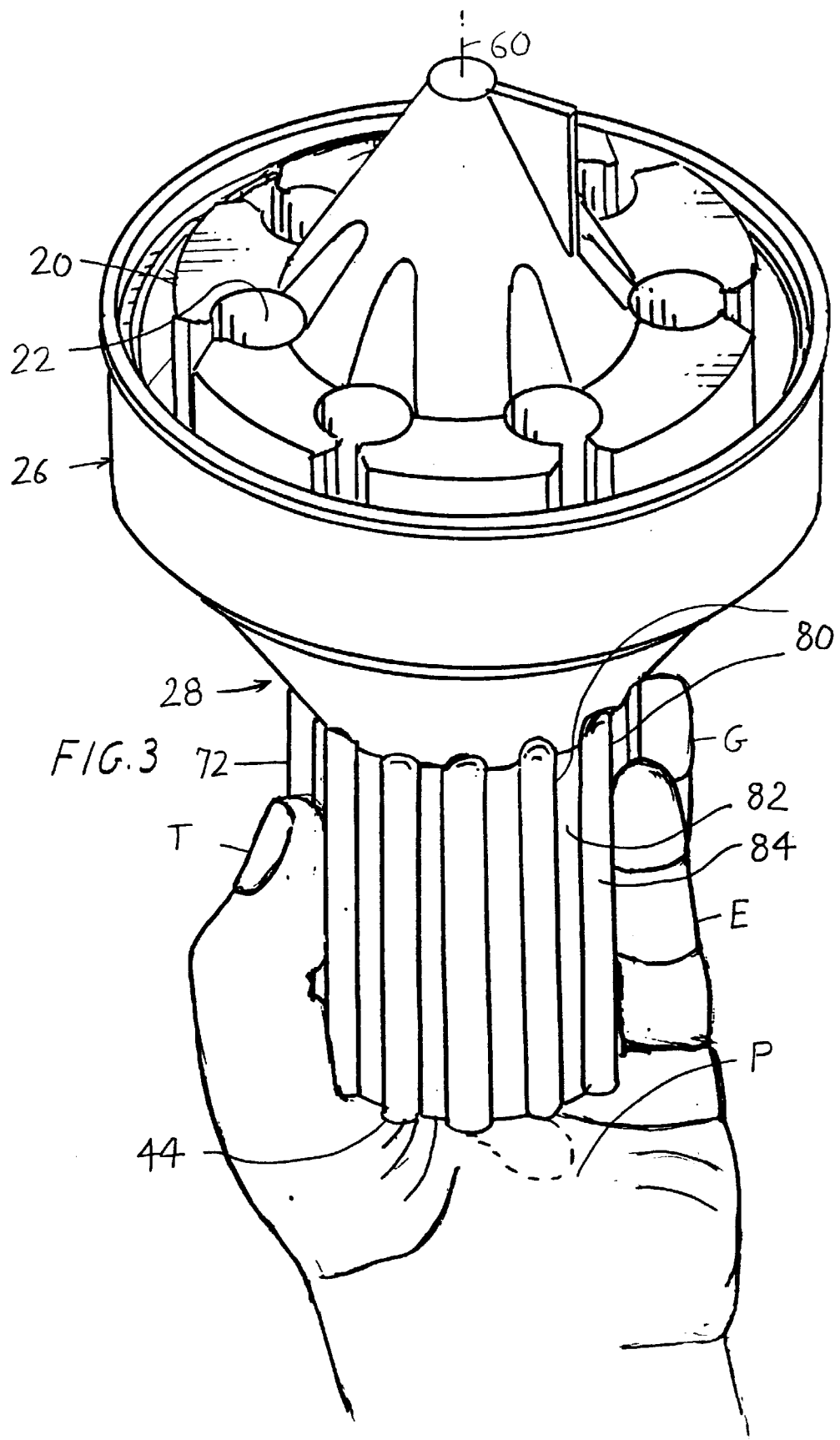
FIG. 3 is an assembled isometric view of the dispenser mechanism of FIG. 2, and showing a person properly grasping the handle.

FIG. 3 shows that the outside of the handle has undulations 80 including vertical grooves 82 and vertical projections 84 between the grooves. The undulations are preferably spaced apart by at least 1.5 cm to enable adjacent fingers of the hand to lie in adjacent grooves 82. As shown in applicant's FIG. 6, the particular handle 72 has twelve undulations 80 angled 30° apart, and providing undulations with recesses 82 spaced apart by 1.7 cm. The handle device is an injection molded device, with the walls forming the handle 72 being of uniform thickness and undulating in diameter along its outside and inside.

Figure 6:
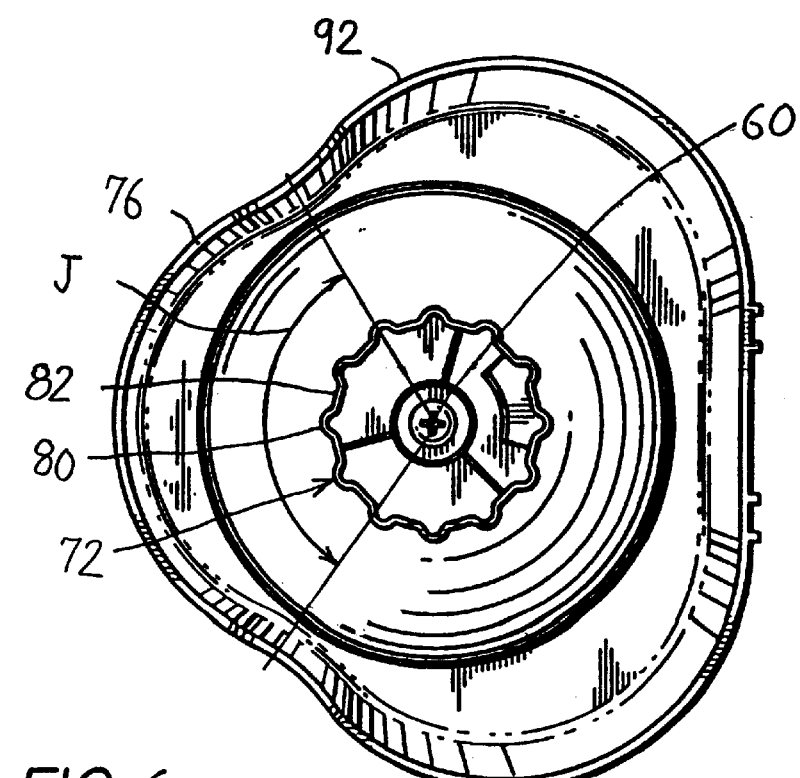
FIG. 6 is a bottom view of the dispenser of FIG. 1, but without the catch pad in place.

Despite the handle construction to minimize the dropping of earplugs, earplugs occasionally drop out of the handle and are not caught by the palm of a person's hand. To prevent such an uncaught earplug from falling onto a dirty floor and being discarded, applicant provides a catch pad 74 shown in FIG. 1, which lies perhaps 10 cm below the bottom of the handle. The stand 16 extends upward from the catch pad to a stand top 90 that supports the lip 62 of the barrier 26. The stand has an access opening 76 through which a person inserts a hand to turn the handle 72. As shown in FIG. 6, the opening 76 extends by an average angle J of about 75° about the vertical axis 60 of the dispenser. It is preferable that the side walls 92 of the stand extend by more than 180° around the axis, to minimize the number of lost earplugs, with the average access opening angle J of 75° leaving the walls 92 to extend 285° about the axis.

The container 12 shown in FIG. 1, is preferably a transparent container that is generally in the shape of a water bottle of the type used on a home water dispenser, but smaller. As shown in FIG. 4, the container 12 has a lower end forming a neck 100 with threads 102 on its outside. The barrier 26 is largely in the form of an upside-down cap, with a circular upstanding wall 104 having internal threads 106. With the container lying upside down, so its open lower end 110 is lowermost, the container is threadably coupled to the upstanding walls of the barrier. This securely mounts the container on the barrier and therefore on the stand, and also seals the container to keep in the earplugs and feed them onto the wheel 20. To connect the container to the rest of the dispenser, the container is placed with its lower end uppermost, the dispense mechanism 14 is turned upside down, and the outside wall of the barrier is turned to screw it to the container. Then, the container with the dispense mechanism attached to it, is turned upside down, and the barrier is laid in a hole 112 at the top of the stand, with the lip 62 of the barrier lying on a surface of the stand.

As shown in applicant's FIG. 4, there is a minimal gap 120 between the bottom of the wheel 20 and the flat upper face 122 of the barrier wall 40. There is no barrier between the wheel 20 and barrier wall 40 to prevent a downward cascade of earplugs 24 through a wheel hole 22 and down through the barrier dispense aperture 42. Each earplug front portion (that fits in an ear canal) has a diameter Q of about 1 cm, while each hole 22 has a diameter of about 2 cm. In the past, as shown in applicant's previous application PCT/US93/09801 (WO 94/09456) and U.S. Pat. No. 5,322,185 (shown in FIG. 6 thereof) applicant provided a cascade barrier to block the area above the hole 22 that lay directly over the dispense aperture 42. Applicant has found that with the use of elastomeric foam earplugs, especially those of slow recovery material, that the earplugs tend to jam themselves in a pile, so that there is no cascade. Instead, the rotation of the wheel past the largely stationary mass of earplugs above the wheel, stirs up the earplugs so one at a time tend to fall into the hole 22 as the wheel is rotated and there is no cascade down through the hole. Because of the high resilience of the earplugs, applicant places the wheel flat lower face 130 very close to the flat upper face 132 of the barrier wall to resist the trapping of earplugs between them. The length M of the gap is preferably no more than 2 mm and more preferably no more than 1 mm to prevent an earplug from entering the gap and jamming under it. Similarly, the average width of the gap 134 between the outside of the wheel and the inside of the container is preferably no more than 3 mm to prevent the jamming of an earplug in this gap. However, a gap 134 that is, on average, at least 1 mm is generally necessary to account for tolerances in the inside diameter of the container and the outside of the wheel.

Thus, the invention provides an earplug dispenser of relatively simple design and easy operation, which resists the loss of earplugs. The dispenser includes a dispense mechanism with a barrier having a horizontal barrier wall having a dispense aperture, a wheel with holes that is rotatably mounted above the barrier wall, and a handle device that is rotatably mounted below the barrier wall and connected to the wheel. The handle device includes a handle with substantially vertical (angled no more than 20° from the vertical) handle walls having a vertical height that is more than half the diameter of the handle. The handle diameter is preferably between 4 cm and 9 cm, and the height is preferably at least 4 cm. This encourages a person to place his/her palm closely under the open bottom end of the handle and with the fingers extending upwardly along the outside of the handle, to turn the handle and catch an earplug in the palm. The handle has vertical grooves at a pitch of at least 1.5 cm to receive the fingers. A stand that extends downwardly from the barrier and under the handle, has a catch pad at its lower end, and has side walls extending more than 180° about the axis of rotation of the handle to help capture any fallen earplug. The barrier forms a container cap with upstanding walls that are threaded, and that are threadably engaged with an open lower end of a container that holds numerous earplugs.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug dispenser comprising a wheel that is rotatable about a vertical axis and that has a plurality of holes for holding earplugs, with said holes spaced from said axis to move along a circular path as said wheel rotates, a barrier that has a barrier wall lying below said wheel with said barrier wall having a dispense aperture lying below said circular path, and a handle device that is connected to said wheel and that includes a largely vertical passage for receiving earplugs that have fallen through said dispense aperture, with said handle device forming a handle for turning the handle device and wheel, with said vertical passage extending through said handle and said handle having an open lower end, wherein:

said handle has a diameter and has substantially vertical outside handle walls having a vertical height that is more than half said handle diameter, whereby to enable a person's palm to lie close to the bottom of the handle while comfortably turning the handle.

2. The dispenser describe in claim 1 including:

a stand extending downwardly from said barrier with said stand having a lower end, and a catch pad mounted on said stand lower end and extending under said handle to catch any falling earplug;

said stand has stand walls extending about said axis, with an access opening in said stand walls to allow a person to insert the person's hand through the opening to grasp and turn the handle, with said walls extending more than 180° around said axis to avoid the loss of an earplug.

3. The dispenser described in claim 1 including:

an earplug container which has a threaded opening;

said barrier is in the form of an upside-down cap, forming an upwardly-extending circular cap wall with threads thereon;

said container lies upside-down with said threaded opening lying lowermost, and with said threaded opening threadably engaged with said circular cap walls.

4. The dispenser described in claim 1 wherein:

said handle has a primarily cylindrical outer surface of a diameter between 4 cm and 9 cm, and with between 6 and 18 undulations in said outer surface, with each undulation forming a vertically extending projection and a vertically extending groove, with the grooves spaced so adjacent grooves can each receive a different finger of a person's hand.

5. A combination of an elastomeric foam earplug having a front end of an average diameter of about 1 cm, and an earplug dispenser, wherein said earplug dispenser comprises a wheel that is rotatable about a vertical axis and that has a plurality of holes for holding earplugs, with said holes spaced from said axis to move along a circular path as said wheel rotates, a barrier that has a barrier wall lying below said wheel with said barrier wall having a dispense aperture lying along said circular path, and a handle device that is connected to said wheel and that is hollow with an open upper end for receiving earplugs that have fallen through said dispense aperture, and with an open lower end and with said handle device forming a handle for turning the handle device and wheel with the same hand that catches the earplug falling through said open lower end, wherein:

said barrier wall has a substantially flat upper face and said wheel has a substantially flat lower face that lies facewise adjacent to said barrier wall upper face with any gap between them being no more than 2 mm.

6. The combination described in claim 5 wherein:

said handle has substantially vertical outside side walls of a height of at least 4 cm.

7. The combination described in claim 6 wherein:

said handle outside side walls are primarily in the shape of a cylinder of a diameter between 4 cm and 10 cm and with between 6 and 18 vertical groove spaced at a pitch of at least 1.5 cm for receiving fingers of a hand.

8. The dispenser described in claim 5 wherein:

said barrier has an upstanding wall with internal threads; and including a container that surrounds the top of said wheel and that has an open lower end with external threads that are threadably engaged with the threads of said barrier.

9. An earplug dispenser comprising:

a stand and barrier assembly, including a barrier having a horizontal barrier wall with a vertical dispense aperture;

a wheel lying on top of said barrier wall and rotatable about a vertical axis with respect to said barrier, said wheel having a plurality of vertical through holes;

a handle device lying under said barrier wall, said handle device being fixed to said wheel and being rotatable with respect to said barrier;

said handle device being hollow and having an open upper end for receiving an earplug that has fallen through said dispense aperture and having an open lower end, with said handle having a lower part forming a largely cylindrical tube that forms a handle that can be turned by a hand that catches the earplug falling through the open lower end;

a container having an open lower end that is threaded;

said barrier having an upwardly extending circular wall that is threaded and that is detachably threadably engaged with said container lower end.

10. The dispenser described in claim 9 wherein:

said largely cylindrical tube has an outside radius and has a height that is greater than said radius.

11. The dispenser described in claim 9 wherein:

said stand extends below said handle device, and said stand has walls extending around said handle device but with an access opening to allow a person to insert a hand therethrough to grasp and turn the handle, with said walls extending at least 180° around a location below said handle to avoid the escape of a fumbled earplug.

* * * * *